United States Patent [19]

Zhang et al.

[11] Patent Number: 5,686,261
[45] Date of Patent: Nov. 11, 1997

[54] XANTHYLIUM DYES THAT ARE WELL RETAINED IN MITOCHONDRIA

[75] Inventors: Yu-Zhong Zhang; Richard P. Haugland, both of Eugene, Oreg.

[73] Assignee: Molecular Probes, Inc., Eugene, Oreg.

[21] Appl. No.: 383,298

[22] Filed: Feb. 3, 1995

Related U.S. Application Data

[63] Continuation-in-part of Ser. No. 143,440, Oct. 25, 1993, Pat. No. 5,459,268.
[51] Int. Cl.$^6$ .................. C12Q 1/02; C12Q 1/68
[52] U.S. Cl. .................. 435/405; 435/6; 435/7.21; 435/7.24; 435/7.31
[58] Field of Search .................. 435/6, 7.21, 40.5, 435/7.24, 7.31

[56] References Cited

U.S. PATENT DOCUMENTS 5,321,130  6/1994  Yue et al. .................. 436/800

FOREIGN PATENT DOCUMENTS

| | | |
|---|---|---|
| WO93/04077 | 3/1993 | WIPO . |
| WO93/04192 | 3/1993 | WIPO . |
| WO93/06482 | 4/1993 | WIPO . |
| WO94/24213 | 10/1994 | WIPO . |

OTHER PUBLICATIONS

Richard P. Haugland, Molecular Probes, Handbood of Fluorescent Probes and Research Chemicals 1992–1994, Molecular Probes, Inc. (1992). pp. 9–16 1992.

Michael Brinkley, Bioconjugate Chemistry, vol. 3, pp. 2–13 (1992).

Haugland, Molecular Probes Handbook of Fluorescent Probes and Research Chemicals, 1992, Set. 30.

Rothe, et al., Journal of Immunological Methods, 138, 133 (1991).

Martinez, et al., Exp. Cell Res., 164, 551 (1986).

Kliot–Fields, et al., Somatic Cell Genetics, 9, 375 (1983).

Riedy, et al., Cytometry, 12, 133 (1991).

Haugland, Molecular Probes Handbook of Fluorescent Probes and Research Chemicals, 1992, Set 24.

Hahn, et al., J. Histochem. Cytochem., 41, 631 (1993).

*Primary Examiner*—Mary E. Ceperley
*Attorney, Agent, or Firm*—Allegra J. Helfenstein; Anton E. Skaugset

[57] ABSTRACT

The present invention describes a method of staining mitochondria, and analyzing mitochondrial function, using a class of fluorescent substituted 3',6'-diaminoxanthenes and their reduced analogs 3',6'-diaminodihydroxanthenes, which are oxidized to the fluorescent form of the dye in situ. In their oxidized form, the dyes selectively localize within mitochondria. The dyes of the invention are substituted by an alkylating group that allows their retention in mitochondria even after cell death, fixation, and permeabilization.

20 Claims, 1 Drawing Sheet

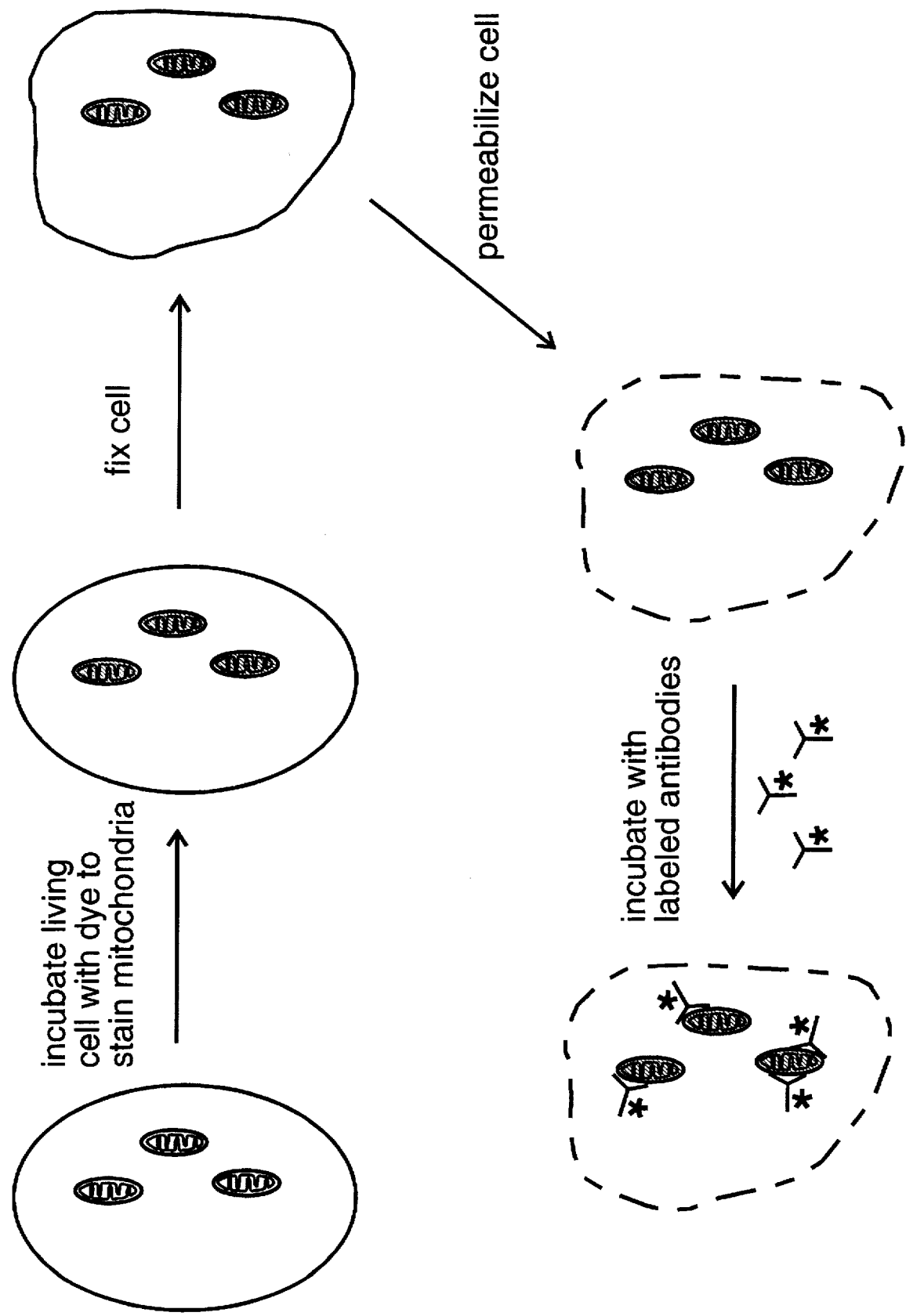

XANTHYLIUM DYES THAT ARE WELL RETAINED IN MITOCHONDRIA

This application is a continuation-in-part of Application Ser. No. 08/143,440 filed Oct. 25, 1993, now U.S. Pat. No. 5,429,268 to Haugland et al. (1995).

FIELD OF INVENTION

The invention relates to fluorescent stains for mitochondria. In particular, the present invention relates to the staining of mitochondria in living cells, or extracellularly, with fluorescent or fluorogenic compounds that are retained within the mitochondria even after cell fixation and permeabilization.

BACKGROUND OF THE INVENTION

Fluorescent dyes are known to be particularly suitable for biological applications in which a highly sensitive detection reagent is desirable. Dyes that are able to preferentially bind to a specific biological ingredient in a sample enable the researcher to determine the presence or quantity of that specific ingredient. In addition, specific cellular structures can be monitored with respect to their spatial and temporal distribution in diverse environments. Furthermore, dyes can be used to determine ionic, electrical or metabolic properties of cellular organelles.

Mitochondria are the intracellular organelles responsible for aerobic metabolism in eukaryotic cells. Their abundance varies with cellular energy level and is a function of cell type, cell-cycle stage and proliferative state. There is a need in biology to detect and observe mitochondria particularly in cells, as a specific application or in conjunction with additional labeling of other components under study. Due to the strong proton gradient across the mitochondrial membrane (alternatively stated, the strong redox potential across the membrane) a variety of substances that possess a cationic charge have been found to selectively localize within functioning mitochondria. Under the proper conditions, this property has been used to localize a variety of fluorescent dyes within mitochondria for use in imaging (Haugland, MOLECULAR PROBES HANDBOOK OF FLUORESCENT PROBES AND RESEARCH CHEMICALS, 1992, Set 30).

There are several "xanthylium" dyes that have proven useful for mitochondrial labeling. The fluorescent dyes tetramethylrosamine, rhodamine 123 and rhodamine 6G are readily sequestered in mitochondria, where localization of the dyes is a function of membrane potential. The reduced forms of these dyes are all colorless diaminodihydroxanthene derivatives, which become fluorescent only upon oxidation to the parent xanthylium dye within living cells. The fluorescent stain that results from intracellular oxidation can then be made to localize within the mitochondria. Furthermore, these mitochondrial stains have been used in conjunction with flow cytometry to sort and/or analyze cells. See, for example Rothe et al., JOURNAL OF IMMUNOLOGICAL METHODS, 138, 133 (1991), Martinez et al., EXP. CELL RES. 164, 551(1986), Kliot-Fields et at. SOMATIC CELL GENETICS, 9, 375 (1983).

While currently available mitochondria stains, such as rhodamine 123 and tetramethylrosamine, are typically used to stain cells in concentrations of approximately 1–2 µM, the dyes of the present invention provide bright mitochondrial staining at much lower concentrations. Typically concentrations between 20 nM and 500 nM are sufficient to give very good fluorescent staining of mitochondria.

All currently available xanthylium stains for mitochondria share a common drawback. The cationic dye is sequestered in the mitochondria in an equilibrium process, and mitochondrial staining can only be maintained by a functioning mitochondria. Attempts to fix stained cells generally result in cell death, the loss of mitochondrial potential, and therefore the loss of mitochondrial stain. Cells that are killed before staining do not stain well, again due to the lack of potential across the mitochondrial membrane. This is a drawback for researchers wishing to investigate mitochondrial function or viability in pathogenic species, who must choose between the very poor staining procedures available for fixed cells, or the additional hazards and costs associated with handling live pathogens. A method for assessing the viability of pathogenic species by staining with ethidium monoazide, then fixing, has been described (Riedy et at., CYTOMETRY, 12, 133 (1991). Staining with ethidium monoazide, however, only reveals the membrane permeability of the cell at the time of staining, and reveals no information regarding the metabolic state of the cell under investigation. The dyes of the present invention will indicate cells that possessed functioning mitochondria at the time of staining, even after fixation. The assessment of mitochondrial function is a much more meaningful indicator of metabolic activity than membrane permeability.

An additional drawback to the use of xanthylium mitochondrial stains is their incompatibility with the use of other labeling techniques, including immunocytochemical staining of intracellular antigens and in situ hybridization. The use of labeled antibodies, labeled oligonucleotides, or labeled probes for intracellular protein receptors require permeabilization of the cell membranes to allow the bulky labeling agents to enter the cellular space. During fixation and permeabilization, standard mitochondrial stains are washed away. Utilizing the dyes of the current invention, mitochondria can be stained, the cell can be fixed and permeabilized, and a variety of labeling agents can then be utilized for simultaneous visualization of mitochondria and other cellular components.

The dyes of the present invention are cationic fluorescent xanthylium dyes that localize within the mitochondria of living cells, and are retained there. The reduced diaminodihydroxanthene forms of the present dyes are oxidized intracellularly or within mitochondria to the fluorescent xanthylium form of the dyes, which then localize within the mitochondria. While previous examples of mitochondrial stains can localize within mitochondria, they are not retained as effectively as the dyes of the present invention. For example, cells that have been stained with rhodamine 123 can lose fluorescent staining in about 30 minutes when put into fresh medium that does not contain rhodamine 123. One of the most effective mitochondrial stains, tetramethylrosamine, maintains staining for only about 6–12 hours, depending on the concentration of the labeling solution used. In either case, essentially all mitochondrial staining is lost upon fixation of the sample cells. A major advantage of the present dyes lies in their long-term retention within the mitochondria, even through cell division, or after fixation and permeabilization of the sample cells. This retention is due to the presence of an alkylating group attached to the dye that reacts with intracellular nucleophiles, including thiols, to form a conjugate. This conjugate is retained within the mitochondria, and is not removed by washing or even after washing fixed and permeabilized cells.

The use of a haloalkyl functional group to retain a fluorescent reaction product of enzymatic activity within a cell has been described in the PCT Application USE OF HALOALKYL DERIVATIVES OF REPORTER MOLECULES TO ANALYZE METABOLIC ACTIVITY IN CELLS, by Haugland et al., Int. Publ. No. WO 93/04192. The reagents described in the reference contain a blocking group removed by the activity of a selected enzyme and a haloalkyl group that reacts with an intracellular thiol to retain the reagents in the cell. The reagents are substrates for selected enzymes and become fluorescent, or more fluorescent, after being acted upon by that enzyme. A haloalkyl functional group present on the substrate reacts with an intracellular thiol to give a fluorescent product that is retained within the cell even after washing or fixation. Exemplified and specifically described compounds of the above reference are retained within the cytoplasm of sample cells, but do not localize within the mitochondria of the cells. There is no indication that the compounds described in the reference localize in the mitochondria, or in any other organelle.

A specific haloalkyl derivative of a xanthylium reporter molecule, chloromethylbenzoylaminotetramethylrhodamine, is currently available from Molecular Probes Inc. (Haugland, HANDBOOK OF FLUORESCENT PROBES AND RESEARCH CHEMICALS, 1992, Set 24, under the trade name CellTracker™ Orange CMTMR). Unlike the mitochondria stains of the present invention, the overall charge of chloromethylbenzoylaminotetramethylrhodamine is neutral, and it does not localize in mitochondria.

It is an object of this invention to provide new fluorescent stains that are well-retained in mitochondria, particularly in the mitochondria of eukaryotic cells. It is further an object of this invention to use these materials to assess the mitochondrial function in eukaryotic cells, in particular, the assessment of mitochondrial function as it relates to the viability of eukaryotic cells. The assessment of mitochondrial function at the time of staining can then be carried out even after fixation of the cell. In conjunction with the mitochondrial stains of the invention, the mitochondria or cells can be stained with an additional detection reagent, such as a labeled antibody, labeled oligonucleotide, or other indicator for a specific cellular component or substructure.

DESCRIPTION OF THE DRAWINGS

FIG. 1. A graphic depiction of the utility of the dyes of the present invention as described in Examples 14 and 15. Staining of the mitochondria in a living cell is followed by fixation, permeabilization, and incubation with an additional detection reagent without loss of mitochondrial stain.

SUMMARY OF THE INVENTION INCLUDING DESCRIPTION OF PREFERRED EMBODIMENTS

Description of the Dyes

The dyes of the present invention are xanthylium or xanthene dyes that in their oxidized forms contain both a cationic charge and an alkylating group. The dyes are fluorescent or readily become fluorescent upon oxidation in mitochondria or in living cells. Under appropriate conditions, these dyes are retained in the mitochondria of living cells.

The preferred dyes of the present invention are substituted 3',6'-diaminoxanthenes (formula I) and substituted 3',6'-diaminodihydroxanthenes (formula II), as depicted in the following structures:

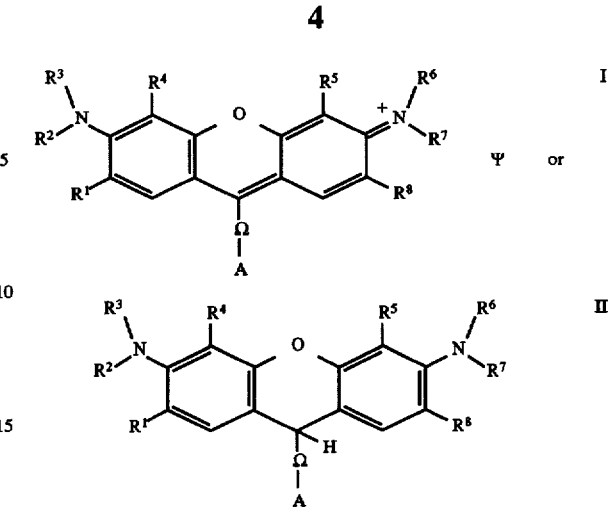

The dyes of formula I and formula II are readily interconvertible by chemical or biological oxidation or reduction. When dyes of formula II are introduced into living cells, they are readily converted to fluorescent dyes of formula I.

The dyes can be described in three parts: The xanthene or xanthylium ring system, the alkylating group (A), and the covalent linkage (Ω) that joins the alkylating group to the ring system.

The Xanthene or Xanthylium Ring System

The xanthene or xanthylium ring system contains ring substituents $R^1$, $R^4$, $R^5$ and $R^8$ and amino substituents $R^2$, $R^3$, $R^6$ and $R^7$. Adjacent pairs of amino and ring substituents are optionally separate, or combine to form additional fused rings.

The xanthene or xanthylium ring system is a substituted 3',6'-diaminoxanthene or substituted 3',6'-diaminodihydroxanthene. It is well known that the substituents present on a xanthylium ring system will effect the spectral properties of the resulting dye, specifically the excitation or emission wavelength and fluorescence yield. In particular, derivatives for which the substituents on the xanthylium system are predominantly hydrogen atoms tend to absorb light maximally at about 490 to 520 nm and to emit green fluorescence. Derivatives that possess extra fused rings tend to have long wavelength spectral properties with orange to red fluorescence. In the case of derivatives for which the predominant number of substituents on the nitrogen atoms are $C_1$ to $C_6$ alkyl groups or a combination of $C_1$ to $C_6$ alkyl groups and hydrogen atoms, the fluorescent emission is typically in the yellow to orange wavelengths.

The ring substituents $R^1$, $R^4$, $R^5$, and $R^8$ are independently H, Cl, Br, I, an alkyl chain $(CH_2)_nCH_3$ or alkyl carboxylate $(CH_2)_nCO_2R^{13}$, where n is an integer between 0 and 15 and $R^{13}$ is an alkyl with 1–6 carbons. Typically $R^{13}$ is $CH_3$. Typically, $R^1$, $R^4$, $R^5$, and $R^8$ are H or $CH_3$. The amino substituents $R^2$, $R^3$, $R^6$, and $R^7$ are independently H or $C_1$ to $C_6$ alkyl. Typically, the amino substituents $R^2$, $R^3$, $R^6$, and $R^7$ are $CH_3$ or $C_2H_5$.

Alternatively, amino substituents combine with ring substituents such that one or more pairs of substituents $R^1$ and $R^2$, $R^3$ and $R^4$, $R^5$ and $R^6$, $R^7$ and $R^8$, when taken in combination are optionally and independently two or three methylenes, each pair optionally forming a 5- or 6-membered ring that is fused to the xanthene ring system. Preferred embodiments of the invention are xanthylium or xanthenes substituted by four 6-membered fused rings according to III and IV as shown below.

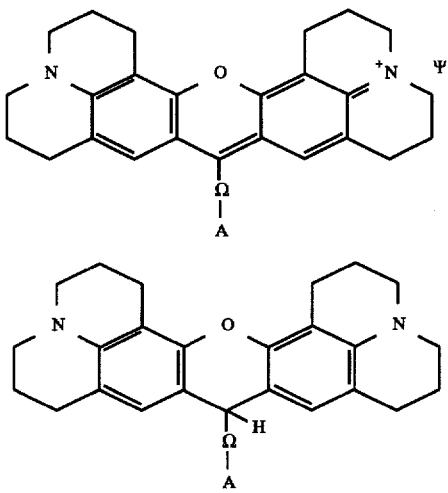

III

IV

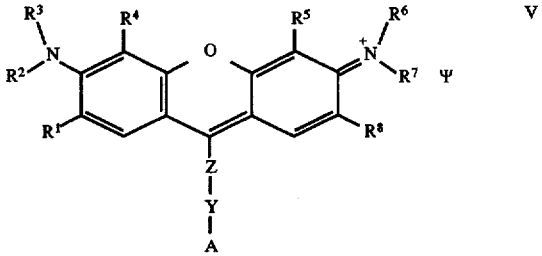

V

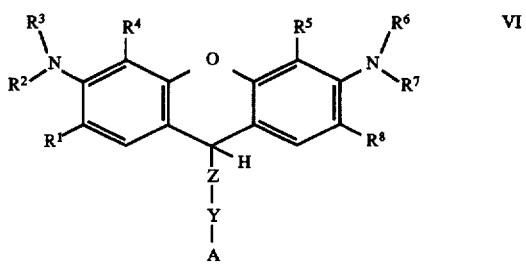

VI

To achieve selective localization of the dyes of the present invention by the mitochondria requires that the overall charge of the reactive xanthylium dye is positive. Xanthylium dyes in which the charge is neutral or negative do not function in this application and are specifically excluded in this invention (xanthene dyes of this invention, however, are neutral until oxidized to the xanthylium form). The necessary positive charge present on the xanthylium dyes of the invention is balanced by the presence of a biologically compatible counterion, which is indicated by the symbol Ψ. As used herein, a biologically compatible counterion is not toxic as used, and does not have a substantially deleterious effect on biomolecules. Examples of Ψ include, among others, chloride, bromide, iodide, sulfate, alkanesulfonate, arylsulfonate, phosphate, perchlorate, tetrafluoroborate, tetraphenylboride, nitrate and anions of aromatic or aliphatic carboxylic acids. Preferred Ψ counterions are chloride, iodide, perchlorate and various sulfonates.

The Alkylating Group

The alkylating group, A, is a reactive site which will react, either directly or through the action of an enzyme, with intracellular nucleophiles. Typically the intracellular nucleophile is a thiol such as glutathione or a cysteine-containing protein.

Preferably A has the formula —$CR^9R^{10}$—X, where $R^9$ and $R^{10}$ are independently H or $CH_3$, typically both $R^9$ and $R^{10}$ are H. X is a labile substituent that is Cl, Br, or I. Alternatively X is a sulfonate ester —$OSO_2R^{16}$, where $R^{16}$ is an alkyl with 1–6 carbons, a perfluoroalkyl with 1–6 carbons, phenyl, or $R^{16}$ is a phenyl substituted one or more times by an alkyl with 1–6 carbons, perfluoroalkyl with 1–6 carbons, Cl, Br, I, $NO_2$ or CN. Typically, X is a halogen, preferably X is Cl.

Alternatively, A is maleimidyl (—$NC_4H_2O_2$) or haloacetamido (—NH(C=O)—$CH_2$II) where II is Cl, Br or I.

The Covalent Linkage

The alkylating group is attached to the ring system by any appropriate covalent linkage (Ω). Examples of Ω include, but are not limited to, a single covalent bond, or a variety of spacers and linking groups, as described below.

The linkage Ω optionally is a single covalent bond or includes a linking group (Z) or a spacer (Y) or both, such that Ω is represented as —Z—Y—. Both Z and Y are covalently attached. When Ω is in the form —Z—Y—, either of Z or Y, but not both, is optionally a covalent bond. In one embodiment, Y is a covalent bond. When Ω is described in the form —Z—Y—, the dyes of the present invention are represented as shown in Formula V and Formula VI, below.

Examples of Z include, but are not limited to, an alkylene (—$(CH_2)_n$—, n=1–6), a phenylene, or an alkyl carboxylate substituted (—$CO_2R^{11}$) phenylene, where $R^{11}$ is an alkyl with 1–6 carbons. The alkyl group $R^{11}$ may be a branched, unbranched, saturated or unsaturated alkyl. In one embodiment, Z is a phenylene or substituted phenylene linking group. When Z is a phenylene linking group, Z is preferably para substituted. When Z is an alkyl carboxylate substituted phenylene linking group, the alkyl carboxylate is preferably attached ortho to the point of attachment of the phenylene linking group to the xanthene ring.

Y is a covalently linked spacer. Typical Y spacers are —$(CH_2)_n$—(n=1–6), —$SO_2$, —$OCH_2R^{12}$—, —$OR^{13}$, —$SR^{12}$—, —$SR^{13}$—, —$NHCOCH_2R^{12}$—, —$NHCOR^{13}$—, —$CONHCH_2R^{12}$—, —$CONHR^{13}$—, $NHSO_2R^{12}$—, —$NHSO_2R^{13}$—, —$NHCONHCH_2R^{12}$—, —$NHCONHR^{13}$—, —$NHCSNHCH_2R^{12}$—, or —$NHCSNHR^{13}$—, where $R^{12}$ is $(CH_2)_m$ and m=1–18, and $R^{13}$ is phenylene (—$C_6H_4$—).

Synthesis of Materials

In general, synthesis of the xanthylium dyes and diaminodihydroxanthenes involves the reaction of at least two equivalents of an appropriately substituted m-aminophenol derivative

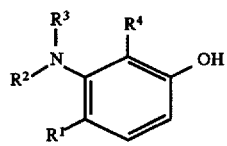

(where $R^1$, $R^2$, $R^3$ and $R^4$ are defined as above)

with one mole of an aldehyde (Q-CHO) or a carboxylic acid derivative (Q-$COR^{14}$). The substituent $R^{14}$ is OH, a halogen, or the elements needed to yield an ester (such as a methyl ester) or an anhydride (such as a mixed anhydride). The group Q either incorporates the desired components of —Ω—A directly, or Q incorporates the reactive functional group necessary for preparation of —Ω—A, as describe below.

The reaction is usually catalyzed by an acid such as sulfuric acid, methanesulfonic acid, hydrochloric acid, phosphoric acid, polyphosphoric acid, or a lower alkanoic or perfluoroalkanoic acid such as propionic acid or trxifluoroacetic acid. Alternatively, the reaction is catalyzed by a Lewis acid salt such as zinc chloride. When the reactant is Q-CHO the initial product is a diaminodihydroxanthene:

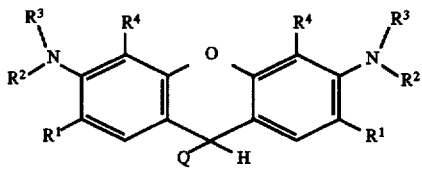

In particular, when Q-CHO is a substituted benzaldehyde, the initial product is termed a "diaminodihydrorosamine." When the reactant is a Q-COR$^{14}$ derivative, the initial product is a xanthylium dye:

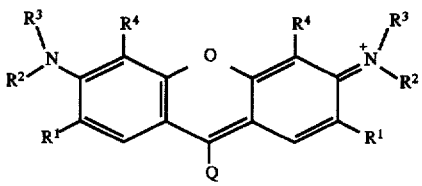

In particular when Q-COR$^{14}$ is a derivative of phthalic acid or phthalic anhydride, the initial products are termed "rhodamines." A large number of rhodamines and methods for their synthesis have been described in the literature. To obtain the ester of the rhodamine the initial acid form of the rhodamine is esterified under suitable conditions well known in the art that include reaction with an alcohol and a mineral acid catalyst, or treatment with a diazoalkane.

Due to the relative ease of synthesis, derivatives of Q for which Q=—Z—CR$^9$R$^{10}$—X or —Z—Y—CR$^9$R$^{10}$—X typically have Z being phenylene or carboalkoxy-substituted phenylene. Analogous chemistry using aliphatic acids or aldehydes yield products in which Z is alkylene.

Due to synthetic simplicity, generally $R^1=R^8$, $R^2=R^7$, $R^3=R^6$, and $R^4=R^5$. However, methods for synthesis of asymmetric derivatives exist. Typically an initial reaction of the appropriately substituted m-aminophenol with Q-CHO or Q-COR$^{14}$, under controlled stoichiometry, followed by reaction with one equivalent of a second appropriately substituted m-aminophenol derivative will yield the desired unsymmetric substitution in the resulting xanthene or xanthylium.

The means for obtaining the alkylating group A, necessary for immobilization of the dye in the mitochondria, depends on the other reactive sites present on the molecule. Typically the alkylating group is either introduced directly as part of Q-CHO or QCOR$^{14}$ with reagents of the form A—Ω—CHO or A—Ω—COR$^{14}$. More commonly, the alkylating group is added by subsequent modification of reactive functional groups present in Q. Examples of such cases where A=—CR$^9$R$^{10}$X include the following:

1. When Q contains a carboxylic acid derivatives, the acid group can be reduced to a hydroxymethyl moiety (R$^9$ and R$^{10}$=H, X=OH). The hydroxyl group can then be converted to chloro (using HCl, PCl$_3$, SOCl$_2$ or a similar chlorinating agent) to bromo or iodo (with analogous halogenating reagents) or to a sulfonate ester (by reaction with a sulfonyl chloride (R$^8$SO$_2$Cl)).

2. When Q contains a nitro derivative, the nitro group can be converted to an amine by chemical or catalytic reduction, such as with sodium hydrosulfide or hydrogen in the presence of a hydrogenation catalyst. Subsequent reaction of the amine with a reagent such as p-chloromethylbenzoyl chloride yields a product wherein R$^9$ and R$^{10}$=H, X=Cl and Ω is a Y that is —NH(C=O)—C$_6$H$_4$—.

3. When Q contains a reactive carboxylic or sulfonic acid derivative, the acid derivative can be converted to an aminoalkyl halide such as 2-bromoethylamine to yield a product where R$^9$ and R$^{10}$=H, X=Br and Ω is a Y that is —(C=O)NHCH$_2$— or —SO$_2$—NHCH$_2$—.

The diaminodihydroxanthene and diaminoxanthylium derivatives are generally freely interconvertible by chemical oxidation or reduction. Reagents useful for this reduction include borohydrides, aluminum hydrides, hydrogen in the presence of a hydrogenation catalyst, and dithionites. Choice of the reducing agent may depend on the ease of reduction of other reducible groups in the molecule. A wide variety of oxidizing agents mediate the oxidation of the diaminodihydroxanthenes, including molecular oxygen in the presence or absence of a catalyst, dichromate, triphenylcarbenium and chloranil (Examples 4 and 8). The diaminodihydroxanthenes are also oxidized by enzyme action, including the action of horseradish peroxidase.

The biologically compatible counterion Ψ that is necessary to neutralize the positive charge(s) on the xanthylium dyes usually results from the method of synthesis of the dye. If necessary Ψ can be exchanged by means well known in the art, including but not limited to ion exchange chromatography, precipitation in the presence of a large excess of a salt of Ψ or selective extraction or precipitation of the salt with an organic solvent.

The above description and subsequent examples are not intended to fully describe or to limit the possible synthetic routes to the subject materials. Many other reagents and synthetic modifications exist for the incorporation of an appropriate A moiety, either before or after the initial condensation reaction. Similarly, several methods for the interconversion of the diaminodihydroxanthene and xanthylium species will be obvious to one skilled in the art.

Use of the Dyes of the Invention to Stain Mitochondria

The dyes of the present invention are utilized by preparing a labeling solution of the dye, introducing the dye into the sample containing mitochondria, incubating the sample for a time sufficient to produce a detectable fluorescent response, and observing or analyzing the staining pattern in the sample. The sample may be a cell or cells that contain mitochondria or the sample may contain isolated mitochondria (i.e. not incorporated in a cell).

The degree of staining of mitochondria is a reflection of the membrane potential present across the mitochondrial membrane at the time of staining, i.e., whether or not the mitochondria are functioning. While in general functioning mitochondria are an indicator of cell viability, it is possible to render a cell non-viable, while still retaining mitochondrial membrane potential.

Preparation of a Labeling Solution

The pure dyes generally have low solubility in water. Typically a stock solution is prepared by weighing out a known mass of the pure reagent and dissolving the reagent in an organic solvent. Preferred organic solvents are DMSO, dimethylformamide, acetone, acetonitrile, dioxane, tetrahydrofuran and other nonhydroxylic, completely watermiscible solvents. The stock solutions are protected from light at all times and, in the case of diaminodihydroxanthenes, are further protected from air oxidation by purging with a suitable gas such as argon or nitrogen. Additionally, the use of very polar organic solvents should be avoided with diaminodihydroxanthenes, as conversion to the xanthylium form of the dye may occur spontaneously in these solvents. The labeling solution is prepared by diluting an aliquot of the stock solution into aqueous buffer to the desired labeling concentration.

In general the amount of dye added in the labeling solution is the minimum amount required to yield detectable mitochondrial staining in the sample, without significant background fluorescence or staining of other organelles or cellular structures. The amount of reagent required for staining eukaryotic mitochondria depends on the sensitivity required for staining of intracellular vs. cell-free mitochondria, the number of cells present, the permeability of the cell membrane to the reagent and, in the case of the diaminodihydroxanthenes, the time required for intracellular metabolism to generate a fluorescent product. In the case of staining of tissues, the amount of reagent required may also vary with the accessibility of the reagent to the cells in the tissue. The required concentration for the labeling solution is determined by systematic variation in labeling concentration until a satisfactory fluorescent labeling is accomplished. Typically, the amount of fluorescent xanthylium reagent required is about 20 to about 500 nM, more typically about 50 to about 200 nM. Typically the amount of non-fluorescent diaminodihydroxanthene reagent required is about 20 nM to 500 nM, more typically about 75 nM to about 300 nM.

Low concentrations of dye will require longer incubation times for equivalent fluorescent brightness to be reached. Typically cells incubated in 20 nM labeling solution will require about 1 to 2 hours to reach an arbitrary level of fluorescent staining that is reached in about 30 minutes using a 50 nM labeling solution. Similarly, the level of staining reached in 30 minutes using a 75 nM labeling solution of a diaminodihydroxanthene dye will require incubation for 90 minutes in a 50 nM labeling solution.

Staining concentrations greater than 50 nM give good staining of mitochondria in live cells. At higher concentrations of stain, background fluorescence may be high in live cells, but resolution of mitochondria after fixation is improved. At staining concentrations of between 150 nM and 500 nM, the mitochondria are brightly stained after fixation, with little or no background. Staining of isolated (cell-free mitochondria) will typically require lower concentrations of dye.

The exact concentration of stain to be used is dependent upon the experimental conditions and the desired results and optimization of experimental conditions is required to determine the best concentration of stain to be used in a given application.

Staining Sample Mitochondria

The sample optionally comprises cell-free mitochondria or cells that contain mitochondria. Any cells that contain mitochondria can be used, including but not limited to, fresh or cultured cells, cell lines, cells in biological fluids, cells in tissue or biopsy, and yeast cells.

Following preparation of the labeling solution, the solution is combined with the sample being analyzed. The dyes of the present invention are cell permeant, and can be introduced into the sample cell or cells by incubation of the cell or cells in the labeling solution. Any other method of introducing the dye into the sample cell, such as microinjection of a labeling solution, scrape loading techniques (short mechanical disruption of the plasma membrane where the plasma membrane is peeled away from the cytoplasm, the dye is perfused through the sample and the plasma membrane reassembled), or patch clamp methods (where an opening is maintained in the plasma membrane for long periods) can be used. Any other treatment that will permeabilize the plasma membrane, such as electroporation, shock treatments or high extracellular ATP can be used to accelerate introduction of the dye into the cellular cytoplasm. Typically the dye will be introduced into the sample cell by incubation in the labeling solution, or by microinjection. Preferably the dye is introduced in to the cell or cells by incubation in the labeling solution. Microinjection of dye solution is used when analysis of mitochondrial function of a single cell is desired, within a colony of other sample cells.

Because staining with the diaminodihydroxanthene dyes requires oxidation before formation of a highly fluorescent and cationic product, these non-fluorescent compounds can indicate the metabolic rate of mitochondria. For samples containing cells, the rate of staining with a diaminodihydroxanthene reagent depends on, and is a measure of, the overall metabolic rate of the cell and may vary considerably within otherwise identical cells or between different cells. A healthy cell in culture, on a microscope slide or suspension will typically exhibit visibly-stained mitochondria within about 30 minutes when stained with a 50 nM labeling solution of a diaminodihydroxanthene reagent.

A number of reagents and conditions are known to effect the mitochondrial membrane potential and the metabolism by mitochondrial enzymes. Constituents of the growth medium such as glucose increase the metabolic rate, which includes oxidation of the diaminodihydroxanthenes to xanthylium dyes. In contrast, mitochondrial uncouplers such as 2,4-dinitrophenol, KCN and CCCP (carbonyl cyanide m-chlorophenylhydrazone) depress the membrane mitochondrial potential resulting in decreased uptake of cationic dyes. Staining of cells in the presence of 20 µM CCCP results in 75–100% less mitochondrial fluorescence than is present in comparable cells stained in the absence of CCCP (Example 18). Similarly, staining of cells in the presence of 2,4-dinitrophenol (2,4-DNP) results in about 20% less fluorescent intensity than that present in similar cells stained in the absence of 2,4-DNP.

In the case of the xanthylium dyes, the reduced mitochondrial membrane potential caused by any of these treatments results in decreased uptake of the cationic dyes. For the diaminodihydroxanthenes, a decreased metabolism results in lower conversion of the colorless diaminodihydroxanthene dyes to the fluorescent xanthylium dyes. In either case, the decreased fluorescence can be used to determine the effect of a mitochondrial uncoupler or metabolic change.

The dyes of the present invention are generally non-toxic to living cells and mitochondria. Sample cells have been incubated in 100 nM dye solution for 72 hours without observable ill effects. Stained cells have been observed to undergo cell division, producing daughter cells that also possess stained mitochondria.

Preparation for Observation

The sample can be observed immediately after mitochondrial staining is evident. After staining, the cells or isolated mitochondria in a sample can optionally be fixed. A number of fixatives and fixation conditions are suitable for practicing this invention. Useful fixatives include, but are not limited to, formaldehyde, paraformaldehyde, formalin, glutaraldehyde, cold methanol and 3:1 methanol:acetic acid. Typically, cell fixation is accomplished by incubating in a 3.7% solution of paraformaldehyde for about 15–30 minutes.

Fixation is optionally followed or accompanied by permeabilization, such as with acetone, ethanol, DMSO or various detergents. Permeabilization is utilized to allow bulky additional detection reagents to enter the cellular space (vida infra) that would ordinarily be impermeant with respect to the cellular membrane. A large variety of fixatives, fixation conditions, and permeabilization agents are known in the art, and other methods of fixing or permeabilizing sample cells in conjunction with the stains of the present invention will be obvious to one of ordinary skill. Mitochondria stained by dyes of the present invention retain fluorescent staining even after fixation and extensive permeabilization.

Optionally, the cells or isolated mitochondria are washed to improve the results of the staining procedure. Washing the sample cell or cells after incubation in the labeling solution, or optionally after fixation or permeabilization, greatly improves the visualization of the mitochondria. This is largely due to the decrease in non-specific background fluorescence after washing. Satisfactory mitochondrial visualization is possible without washing at low labeling concentrations (for example <50 nM).

Additional Detection Reagents

The use of the mitochondria stains of the present invention is optionally combined with the use of an additional detection reagent. An additional detection reagent is a reagent that produces a detectable response due to the presence of a specific cell component, intracellular substance, or cellular condition. One or more additional detection reagents may be used in conjunction with the stains of the present invention, before or after fixation and/or permeabilization. The additional detection reagent may be used to stain the entire cell, or a cellular substructure. The fluorescent signal of the mitochondrial stains of the present invention and the detectable response of the additional detection reagent may be observed simultaneously or sequentially. The observation of mitochondrial staining and a detectable response that are spatially coincident indicate that the additional detection reagent is associated with the cellular mitochondria. A variety of measurements can be made within mitochondria in this manner, even when the additional detection reagent does not localize specifically within the mitochondria.

Appropriate additional detection reagents are fluorescent nucleic acid stains. A variety of appropriate nucleic acid stains are known in the art, including but not limited to, Thiazole Orange, ethidium homodimer, propidium iodide, Hoechst 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et at, 1994; or copending application DIMERS OF UNSYMMETRICAL CYANINE DYES CONTAINING PYRIDINIUM MOIETIES Coy Yue et al., Ser. No. 08/043,665, filed Apr. 5, 1993). The use of an appropriate nucleic acid stain in conjunction with the dyes of the present invention can be selected to allow simultaneous observation of mitochondria, nuclear DNA, RNA and/or mitochondrial DNA.

Other appropriate additional detection reagents are any of the fluorescent metal ion indicators described in copending applications REACTIVE DERIVATIVES OF BAPTA USED TO MAKE ION-SELECTIVE CHELATORS (by Kuhn, et al., Ser. No. 07/843,360, filed Feb. 25, 1992) or FLUORESCENT ION-SELECTIVE DIARYLDIAZA CROWN ETHER CONJUGATES (by Kuhn et al., Ser. No. 08/039,918, filed Mar. 29, 1993).

In another embodiment of the invention, an appropriate additional detection reagent is any probe that selectively stains a cellular organelle such as the cell membrane, nucleus, Golgi apparatus, endoplasmic reticulum, endosomes, lysosomes, vacuoles or synaptic vesicles, or is a second mitochondrial probe.

Specific examples of additional detection reagents include fluorescent stains that are specific for acidic organelles. Specifically, LYSOTRACKER™ probes (available commercially from Molecular Probes Inc., Eugene Oreg.) are fluorescent stains that exhibit high selectivity for acidic organelles, such as lysosomes. The dye then accumulates in the organelle, and is fixable therein, allowing simultaneous visualization of both mitochondria and lysosomes in fixed and permeabilized cells. A similar family of organelle probes, the LYSOSENSOR™ probes (also available commercially from Molecular Probes, Inc.) exhibit the same selectivity as the LYSOTRACKER dyes, but also possess pH-dependent spectral properties within the acidic organelle, allowing them to act as internal pH indicators.

In one embodiment, the additional detection reagent comprises: a) one member of a specific binding pair or a series of specific binding pairs, and b) a means for producing a detectable response. A specific binding pair member can be a ligand or a receptor. As used in this document, the term ligand means any organic compound for which a receptor naturally exists or can be prepared. A receptor is any compound or composition capable or recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse and pesticides. Ligands and receptors are complementary members of a specific binding pair, each specific binding pair member having an area on the surface or in a cavity which specifically binds to and is complementary with a particular spatial and polar organization of the other.

Representative specific binding pairs are shown in Table 2.

TABLE 2

| REPRESENTATIVE SPECIFIC BINDING PAIRS | |
|---|---|
| antigen | antibody |
| biotin | avidin (or streptavidin) |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)† |

*IgG is an immunoglobulin
†aDNA and aRNA are the antisense (complementary) strands used for hybridization The additional detection reagent may be used in conjunction with enzyme conjugates to localize cellular receptors; to localize hybridization probes; or to probe cells and tissues that do not express the enzyme, for example, by enzyme-linked immunosorbent assay (ELISA), or enzyme-mediated histochemistry or cytochemistry, or other enzyme-mediated techniques. Enzyme-mediated techniques take advantage of the attraction between specific binding pairs to detect a variety of analytes.

In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a "complementary conjugate". Alternatively, multiple specific binding pairs may be sequentially linked to the analyte, the complementary conjugate, or to both, resulting in a series of specific binding pairs interposed between the analyte and the detectable enzyme of the complemetary conjugate incorporated in the specific binding complex. Table 3 shows the representative examples of specific binding complexes with and without additional specific binding pairs interposed between the complementary conjugate and the analyte.

translated on cytoplasmic ribosomes and imported into the mitochondria in a subsequent step. The proteins that have their final destination in the mitochondria are usually synthesized as longer precursors with an amino terminal extension, or a "leader sequence", that targets the protein for importation into the mitochondria. By taking advantage of this existing mechanism for protein import, researchers can clone a specific gene sequence and modify it in such a way that the final product, a polypeptide, will target mitochondria in cultured cells. This foreign protein can then be detected using immunocytochemical methods in combination with the dyes of the present invention. Specifically, a secondary detection reagent specific for the desired foreign protein can be used to determine the presence of the protein, while the dyes of the present invention verify their localization within mitochondria (as described in Example 19).

TABLE 3

REPRESENTATIVE SPECIFIC BINDING COMPLEXES

| ANALYTE | ADDITIONAL PAIRS | | | COMPLEMENTARY CONJUGATE |
|---|---|---|---|---|
| DNA | aDNA--biotin | avidin | | biotin--enzyme |
| DNA | aDNA--antigen | antibody--biotin | avidin | biotin--enzyme |
| DNA | | | | aDNA--enzyme |
| DNA | aDNA--biotin | | | avidin--enzyme |
| DNA | aDNA--hapten* | | | anti-hapten--enzyme |
| RNA | aRNA--hapten* | | | anti-hapten--enzyme |
| RNA | aDNA--biotin | | | avidin--enzyme |
| antigen | mouse antibody anti-mouse--biotin | | | avidin--enzyme |
| antigen | mouse antibody anti-mouse | | mouse anti-enzyme | enzyme |
| antigen | | | | antibody--enzyme |
| antigen | antibody--hapten* | | | anti-hapten--enzyme |
| carbohydrate | lectin--biotin | | | avidin--enzyme |
| receptor‡ | ligand--biotin | | | anti-biotin--enzyme |
| IgG | protein A--hapten* | | | anti-hapten--enzyme |

*a hapten is any group for which there is an antibody, typically low molecular weight molecules such as drugs, dyes, and aromatic molecules
‡for instance a drug receptor, a toxin receptor, peptide receptor, protein receptor or carbohydrate receptor
-- a covalent bond between two reagents, all other bonds are noncovalent The additional detection reagent also incorporates a means for producing a detectable response. A detectable response means a change in, or occurrence of, a parameter in a test system which is capable of being perceived, either by direct observation or instrumentally, and which is a function of the presence of a specifically targeted member of a specific binding pair in a cell sample. Such detectable responses include the change in, or appearance of, color, fluorescence, reflectance; pH, chemiluminescence, infrared spectra, or an electron-rich substrate. Appropriate labels to provide a detectable response include, but are not limited to, a visible or fluorescent dye, an enzyme substrate which produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine).

In one embodiment of the invention, the dyes of the invention are used to aid in the detection of foreign gene products in mitochondria. The mitochondrion is the only organelle present in mammalian cells that possesses its own genetic system and machinery for protein synthesis. Less than 10% of the several hundred known mitochondrial proteins, however, are synthesized on mitochondrial ribosomes; the remaining proteins are encoded by nuclear genes, Observation/Analysis At any time after the sample has been stained, the sample is observed with a means for detecting the detectable response of fluorescent labeled mitochondria, if present. In one embodiment, observation is accomplished using visible microscopy. Preferably, the fluorescently labeled mitochondria are observed after the cell or cells have additionally been fixed and/or permeabilized. Observation of the sample comprises illuminating the stained sample with a wavelength of light appropriate to generate a fluorescent response, and visually examining the sample by use of a microscope, or confocal microscope.

Optionally, the sample is analyzed using instrumentation. For example, analysis of the cell or cells is accomplished by illuminating the stained cell or cells with a wavelength of light appropriate to generate a fluorescent response, and electronically detecting and optionally quantifying the fluorescent emission of the stained mitochondria using an appropriate instrument, such as a fluorometer, fluorescent microtiter plate reader, or a flow cytometer. The use of a flow cytometer optionally includes sorting cells based on their fluorescent response.

Any observation or analysis optionally includes the observation or analysis of an additional detection reagent present in the sample cell or cells, by means generally understood in the art and appropriate for the additional detection reagent utilized.

The examples below are given so as to illustrate the practice of this invention. They are not intended to limit or define the entire scope of the invention.

EXAMPLES

Example 1

Synthesis of 4-carboxydihydrotetramethylrosamine (1)

To a solution of concentrated $H_2SO_4$ and $H_2O$ (3:2, 460 mL in a 2 L round bottom flask) is added 3-dimethylaminophenol (50 g, 360.00 mM) and 4-carboxybenzaldehyde (27.36 g, 182.20 mM). The mixture is stirred under mild reflux for 18 hours. Upon cooling to 0°–5° C., the reaction mixture is neutralized with 90% KOH to pH=7. The resulting precipitate is filtered, washed with $H_2O$ (3×200 mL), saturated NaCl (3×100 mL) and then dried to give crude 1 (70 g). Upon purification by column chromatography on silica gel using ethyl acetate as eluant, essentially pure 1 is obtained.

Example 2

Synthesis of dihydro-4-(hydroxmethyl)tetramethylrosamine (2)

4-Carboxydihydrotetramethylrosamine (1) (5.4 g, 14 mM) and triethylamine (2.1 mL, 15 mM) are dissolved in tetrahydrofuran (THF, 50 mL) under a nitrogen atmosphere and cooled to 0° C. Ethyl chloroformate (1.45 mL, 15.2 mM) is added at once and the mixture is stirred for 35–40 minutes. The mixture is then filtered and cooled to 0° C. $NaBH_4$ (1.26 g, 33.3 mM) in $H_2O$ (15 mL) is then added slowly with efficient stirring over 5 to 10 minutes. The reaction mixture is then immediately poured into cold water (200 mL) and extracted with ethyl acetate (3×100 mL). The extract is washed with saturated sodium chloride (2×50 mL), dried over anhydrous $Na_2SO_4$ and evaporated. The residue is purified by column chromatography using silica gel and eluting with hexane:ethyl acetate (1:1) to give 2 (3.1 g, 60%).

Example 3

Synthesis of 4-chloromethyldihydrotetramethylrosamine (3)

The following compound is prepared:

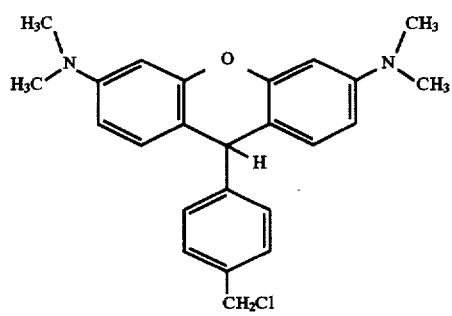

To a stirred solution of compound 2 (1.3 g, 3.5 mM) in dry methylene chloride (15 mL) at 0° C., is added triphosgene (0.43 g, 1.5 mM) in methylene chloride (5 mL) over a period of 5 minutes. This is followed by the addition of pyridine (0.3 mL). The mixture is then brought to room temperature and stirred for an additional 20–25 minutes. The reaction mixture is quenched with water (20 mL) and extracted with $CHCl_3$ (2×25 mL). The organic phase is dried over anhydrous $Na_2SO_4$ and evaporated to give a residue which is purified by column chromatography (silica gel, eluted with hexane:ethyl acetate 3:2) to give 3 (0.2 g, 15%, >98% by TLC). $^1H$ NMR ($CDCl_3$): d=3.0 (12H, s); 4.55 (2H, s);5.1 (1H, s);6.5 (4H, br m); 6.9 (2H, m);7.15 (2H, d);7.3 (2H, d).

Example 4

Synthesis of 4-chloromethyltetramethylrosamine chloride (4)

The following compound is prepared:

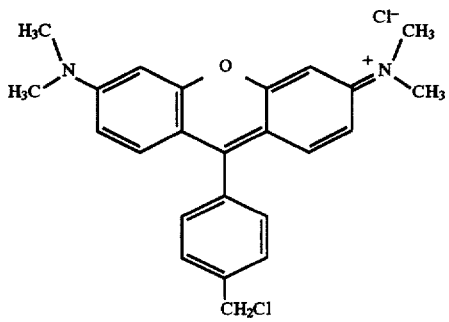

To a stirred solution of 3 (0.2 g, 0.5 mM) in ethanol (5 mL) is added chord (0.125 g, 0.51 mM) and the resulting solution is stirred for 20 minutes at room temperature. The solvent is removed under vacuum and to the residue is added dioxane (5 mL) and 1M HCl (10 mL). A bright reddish-orange fluorescent solution is obtained by brief warming using an electric heating gun for 10 minutes. The clear solution is evaporated to dryness. The resulting residue is dissolved in methanol (2 mL) and the crude solid product is precipitated by adding diethyl ether (15 mL). The solid is filtered and washed with ether. The product is further purified by passing through silica gel and eluting with 20% methanol in $CHCl_3$ to give pure 4 (0.05 g, 20%).

Example 5

Synthesis of 4-carboxydihydro-X-rosamine (5)

This procedure is exactly analogous to that described in Example 1, except that 8-hydroxy julolidine is used in place of 3-dimethylaminophenol.

Example 6

Synthesis of 4-hydroxmethyldihydro-X-rosamine (6)

4-Carboxydihydro-X-rosamine (5) (3.0 g, 6.1 mM) and triethylamine (0.91 mL, 6.7 mM) are dissolved in THF (25 mL) under a nitrogen atmosphere and cooled to 0° C. Ethyl chloroformate (0.64 mL, 6.7 mM) is added at once and the mixture is stirred for 35–40 minutes. After stirring, the mixture is filtered and cooled to 0° C. $NaBH_4$ (0.55 g, 15 mM) in water (5 mL) is then added slowly with efficient stirring over 5 minutes. The reaction mixture is then immediately poured into cold water (100 mL) and extracted with ethyl acetate (3×50 mL). The extract is washed with saturated sodium chloride (2×25 mL), dried over anhydrous Na₂SO₄ and evaporated. The residue is purified by column chromatography using silica gel and eluting with hexane: ethyl acetate (1:1) to give 6 (1.4 g, 48%).

Example 7

Synthesis of 4-chloromethyldihydro-X-rosamine (7)

The following compound is prepared:

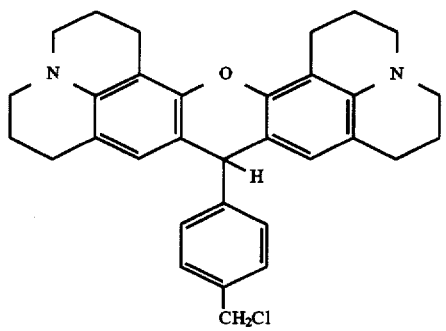

To a stirred solution of triphenylphosphine (0.055 g, 0.21 mM) in dry methylene chloride (5 mL) at 0° C., triphosgene (0.024 g, 0.08 mM) is added over a period of 5 minutes. After the resulting vigorous gas evolution has subsided, the mixture is stirred for an additional 5 minutes. The solvent is removed under reduced pressure, and to the resulting residue is added 4-hydroxymethyldihydro-X-rosamine (6) (0.09 g, 0.2 mM) in dry methylene chloride (3 mL). The mixture is stirred for 20 minutes at room temperature. The solvent is removed under reduced pressure and the residue is extracted with ethyl acetate (2×25 mL). The organic phase is dried over Na₂SO₄ and purification using column chromatography (silica gel, hexane:ethyl acetate 3:2) to give 7 (0.015 g, 16%). ¹H NMR (CDCl₃): d=1.9 (4 H, m); 2.05 (4 H, m); 2.6 (4 H, m); 2.88 (4 H, m); 3.1 (8 H, m); 4.55 (2 H, s); 4.95 (1 H, s); 6.4 (2 H, s); 7.15 (2 H, d); 7.25 (2 H, d).

Example 8

Synthesis of 4-chloromethyl-X-rosamine chloride (8)

The following compound is prepared:

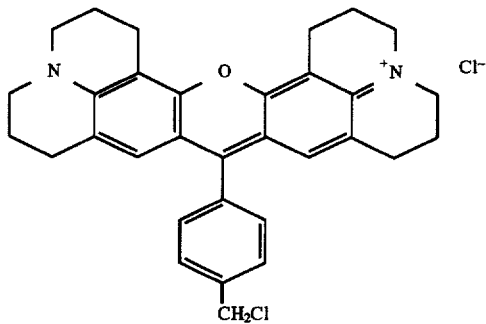

To a stirred solution of 7 (0.6 g, 1 mM) in ethanol (15 mL) is added chloranil (0.295 g, 1.2 mM) and the reaction mixture is stirred for 20 minutes at room temperature. The solvent is then removed under vacuum. To the resulting residue is added dioxane (15 mL) and 1M HCl (30 mL). A bright red fluorescent solution is obtained by warming the mixture using an electric heating gun (10 minutes). The resulting clear solution is evaporated to dryness and the residue is dissolved in methanol (6 mL) and solid product is precipitated by the addition of diethyl ether (50 mL). The solid is filtered and washed with ether. It is further purified by passing through silica gel and eluting with 20% methanol in CHCl₃ to give 8 (0.28 g, 44%).

Example 9

Preparation of 4-((p-chloromethylbenzoyl)amino)tetramethylrosamine (Compound 9)

The following compound is prepared:

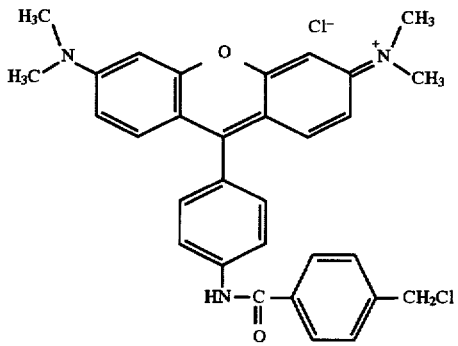

Tetramethyldihydrorosamine carboxylic acid is converted to its NH-BOC derivative by refluxing in t-BuOH for 20 hours in the presence of triethylamine and diphenylphosphoryl azide. The resulting derivative is treated with trifluoroacetic acid, then neutralized with saturated aqueous sodium bicarbonate to give dihydroaminotetramethylrosamine. This intermediate is oxidized using chloranil, as described in Examples 4 and 8, to give aminotetramethylrosamine chloride.

4-chloromethylbenzoic acid is treated with triethylamine and ethyl chloroformate to give the mixed anhydride, which is added to aminotetramethylrosamine chloride in methylene chloride, in the presence of excess triethylamine. Following the amide formation, the reaction mixture is acidified with 1M HCl, then purified using column chromatography to give pure Compound 9.

A comparison between cells stained with Compound 9 and cells stained with the same amount of a closely related dye chloromethylbenzoyl-aminotetramethylrhodamine reveals that chloromethylbenzoylaminotetramethylrhodamine (CellTracker™ Orange CMTMR), which is a neutral species, stains the cell indiscriminately, while Compound 9 (which possesses a positive charge) stains mitochondria selectively.

Example 10

Preparation of 5-((p-chloromethylbenzoyl)amino) tetramethylrhodamine, methyl ester, chloride salt (Compound 10)

The following compound is prepared:

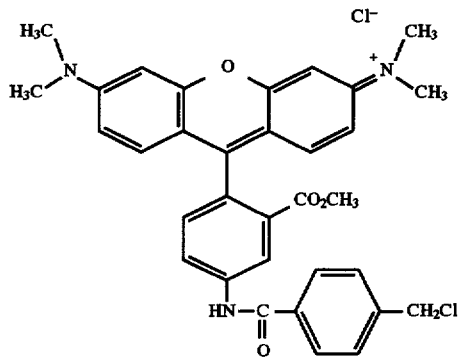

5-Aminotetramethylrhodamine is dissolved in MeOH, in the presence of thionyl chloride, and the solution is heated to reflux. The progress of the methylation is monitored by thin layer chromatography. After conversion to the methyl ester is complete, the crude product is treated with p-chloromethylbenzoyl chloride, to give Compound 10 after chromatographic purification.

Example 11

Synthesis of dihydrotetramethylrosamine-4-(N-(2-bromoethyl)carboxamide)

To a stirred solution of 1 (0.1 g, 0.3 mM) and triethylamine (0.033 g, 0.3 mM) in dry $CH_2Cl_2$ (4 mL) at 0° C., is added ethyl chloroformate over 1 to 2 minutes under $N_2$. The resulting mixture is stirred for 30 minutes at 0° C. The cooling bath is removed and the reaction is brought to room temperature over 30 minutes. The reaction mixture is filtered, washed with $H_2O$ (1×25 mL), saturated NaCl solution (1×25 mL) and dried over anhydrous $Na_2SO_4$. On evaporation of the solution, the resulting anhydride is obtained in essentially pure state and is used without further purification.

To a stirred solution of 2-bromoethylamine (HBr salt) (0.046 g, 0.23 mM) and triethylamine (0.046 g, 0.45 mM) in dry $CH_2Cl_2$ (5 mL) at room temperature is added a solution of the anhydride (0.1 g, 0.2 mM) in $CH_2Cl_2$ (2 mL) under $N_2$. The resulting mixture is stirred for 3 hours at room temperature. It is then diluted with $CHCl_3$, washed with $H_2O$ (2×25 mL), saturated NaCl solution (1×25 mL) and dried over $Na_2SO_4$ (anhydrous). The residue, obtained after evaporation, is chromatographed on silica gel eluting with first 2:1 hexane:ethyl acetate followed by 1:1 hexane:ethyl acetate to give dihydrotetramethylrosamine-4-(N-(2-bromoethyl)carboxamide) (0.03 g, 27%).

Example 12

Preparation of Cell Culture

NIH/3T3 mouse fibroblast cell line is obtained from American Type Culture Collection Co., Rockville, Md. The cells are maintained in a humidified atmosphere of 5% $CO_2$ in Dulbecco's modified Eagle's medium (DMEM) supplemented with 10% calf serum, 50 μg/mL gentamicin, 300 μg/mL L-glutamine and 10 mM HEPES pH 7.4. Cells are subcultured every 3 days by trypsinization using 0.05% trypsin and 0.02% EDTA in a Ca- and Mg-free saline solution (Gibco BRL, Gaithersburg, Md.). Cell passage number ranges from 120–122. To obtain well-spread single cells, 5×10⁴ cells are plated onto 18×18 mm coverslips in 60 mm culture dishes.

Example 13

Preparation of Labeling Solution

Compounds 4, 7 and 8 are separately dissolved in DMSO/ethanol (1/1) to prepare a 5 mM stock solution. The stock solutions are kept sealed in an amber reagent bottle and stored at 4° C. Each labeling solution is prepared by adding stock solution to fresh culture medium in an amount sufficient to make final dye concentrations of between 50 and 200 nM.

Example 14

Labeling of Mitochondria in Live Cells

Cells prepared according to Example 12 are transferred to the labeling medium containing Compound 4 and incubated at 37° C. for 15 to 30 minutes. The cells are then washed with fresh medium and observed using a Zeiss Axioplan microscope equipped with a filter optimized for tetramethylrhodamine.

A comparison between cells stained with 75 nM solutions of tetramethylrosamine and compound 4 respectively shows that both dyes stain mitochondria selectively and fluorescently.

Example 15

Co-localization of Mitochondrial Proteins using Immunocytochemical Assays

The NIH/3T3 cells stained in Example 14 are then fixed in PBS (phosphate buffered saline, Gibco BRL) containing 3.7% paraformaldehyde for 15–30 minutes at room temperature, and washed three times with fresh PBS solution. The cells are then permeabilized with cold acetone (−10° C.) for 15 minutes. The cell sample is examined under a microscope to verify that the mitochondria remain stained with red fluorescence after fixation and permeabilization.

A comparison between cells stained with tetramethylrosamine and cells stained with compound 4 (as in Example 14) shows that upon fixation and permeabilization, cells stained with compound 4 retain fluorescent labeling, while cells stained with tetramethylrosamine lose fluorescent labeling of mitochondria.

After washing with Tris buffered saline (TBS buffer, 3 times, 5 minutes), the cells are incubated with 4% BSA/TBS solution at room temperature for 18 hours. Cells are then washed with TTBS buffer (TBS buffer containing 0.05% Tween 20, 3 times, 5 minutes) and incubated with polyclonal antibodies against the subunit II of cytochrome c oxidase (a mitochondrial protein) in TTBS buffer containing 4% BSA, at room temperature, for 4 hours. Cells are washed with TTBS buffer again (3 times, 10 minutes) and then incubated with goat anti-rabbit IgG, alkaline phosphatase conjugate (1:1000 dilution in TTBS buffer containing 4% BSA), at room temperature, for 2 hours. The cells are washed with TTBS buffer carefully (3 times, 10 minutes). The cells are then incubated with 100 μM 2-(o-hydroxyphenyl) quinoxazolinone phosphate (described in ENZYMATIC ANALYSIS USING SUBSTRATES THAT YIELD FLUORESCENT PRECIPITATES, by Haugland, et al. PCT application no. WO 93/04077), for 30 minutes, at room temperature.

Using a microscope equipped with a long pass filter set and illuminated at 366 nm, the immunoreactive complexes are visible as yellowish-green dots on reddish-orange mitochondria.

Example 16

Labeling of Mitochondria in Peripheral Blood Lymphocytes

Peripheral blood lymphocytes are isolated from whole goat blood. The lymphocytes are stained at three different concentrations of compound 8; 50 nM, 150 nM and 200 nM. The cells are labeled with the appropriate dye concentration, washed, fixed with 3.7% paraformaldehyde, washed again, then permeabilized with acetone.

Lymphocytes stained with 50 mM dye solution exhibit good staining of mitochondria while live. After fixation, much of the mitochondrial staining is lost.

Lymphocytes stained with 150 nM dye solution exhibited good staining of mitochondria while live, with more background fluorescence than observed at 50 nM dye solution. After fixation the background fluorescence is lost, and the mitochondrial stain is very good.

Lymphocytes stained with 200 nM dye solution appear much as those stained with 150 nM dye solution while live. After fixation the resolution of mitochondria is improved over those stained at 150 nM concentrations.

Example 17

Staining of Yeast Cells using Compounds 4 and 8

Live Baker's yeast cells are incubated in an aqueous dye solution that contains 20% glucose and 10 mM HEPES buffer. The living yeast cells are observed using a visible microscope. The sample cells are illuminated at 546 nm and observed at 590 nm.

When stained with a 100 nM labeling solution of Compound 4, live yeast cells exhibit brightly fluorescent mitochondria, with very little background fluorescence. At the same concentration, cells stained with Compound 8 show brightly stained mitochondria, with little background fluorescence.

Example 18

The Effect of Mitochondrial Uncouplers on Staining of Eukaryotic Cells

NIH/3T3 mouse fibroblast cells (See Example 12) are used to test the effect of mitochondrial uncoupler CCCP (carbonyl cyanide m-chlorophenylhydrazone, Sigma Chemicals). Fibroblast cells are subcultured in four dishes (#1–#4) with coverslips, for 24 hours.

A stock solution of CCCP is added to dishes #2 and #4, to provide a final concentration of 20 µM. The cells are incubated at 37° C. for 60 minutes. After initial incubation, Compound 8 is added to dish #1 and dish #2 to a final concentration of 70 nM. Compound 7 is added to dish #3 and dish #4 to a final concentration of 70 nM. All four dishes are incubated at 37° C. for an additional 30 minutes.

The stained cells are washed and observed using a fluorescent microscope coupled to a Photometrics Star-1 cooled CCD camera for quantitative digital imaging. Images are acquired with a 1 second exposure of the CCD. Data are analyzed by sampling the intensity in multiple regions throughout the images of the cells.

The fluorescence of punctate regions in CCCP treated cells is markedly lower than that of the control cells in the absence of CCCP. Moreover, the mitochondrial shape is not clearly defined in the cells treated with the uncoupler.

Relative fluorescence data are shown below:

| Dish | Compound | CCCP | Fluorescence Intensity (arbitrary units) | Background Fluorescence (arbitrary units) |
|---|---|---|---|---|
| 1 | 8 | — | 1200–1800 | 160–170 |
| 2 | 8 | 20 µM | 250–550 | 150–160 |
| 3 | 7 | — | 1300–1500 | 170–180 |
| 4 | 7 | 20 µM | 70–200 | 130 |

Treatment with a mitochondrial uncoupler diminishes the mitochondrial membrane potential and consequently reduces staining of the mitochondria using compound 8 by 75–90%, and reduces staining of the mitochondria using compound 7 by 95–100%

Example 19

Detection of a Foreign Gene Product in Mitochondria

A yeast protein, not normally present in mitochondria, and with a known amino acid sequence, is selected (hereafter referred to as Y1). Monoclonal antibodies are prepared against the Y1 protein. The DNA sequence coded for the selected protein is amplified using the polymerase-chain reaction. The amplified DNA sequences are then fused with amplified, selected bovine nuclear DNA, which codes for bovine heart mitochondrial protein (hereafter referred to as B2). The fused gene then possesses a proper sequence to encode a polypeptide with a correct leader amino acid sequence so as to lead the resulting Y1/B2 fusion protein to be imported into bovine mitochondria.

The fused gene is then ligated into a mammalian expression vector, such as pCI (Promega), which has a proper enhancer/promoter region, and other signal regions for accurate, high efficiency gene expression in bovine cells. Using a mammalian transfection system to transfer the gene construct into cultured bovine cells, a stable transfected cell line is established that expresses the mitochondrial targeting polypeptide Y 1/B2.

The culture cells are stained with a 100 µM solution of compound 8 at 37° C. for 30 minutes, resulting in mitochondrial labeling with red fluorescence. The stained cells are then fixed in 3.7% glutaraldehyde for 20 minutes at room temperature, and permeabilized with cold acetone for 15 minutes. The mitochondrial staining is well retained throughout.

The fixed and permeabilized cells are then incubated with the previously prepared monoclonal antibodies against Y1. The immunocomplexes are detected using fluorescein isothiocyanate (FITC)-labeled secondary antibodies. Illumination and observation of the cell sample reveals bright green fluorescence where the Y1/B2 protein is localized, and red fluorescent mitochondria. The presence of coincident red and green fluorescence, which results in a yellow signal when viewed through a long-pass optical filter, indicates that the Y1/B2 protein localizes within mitochondria.

It is to be understood that, while the foregoing invention has been described in detail by way of illustration and example, numerous modifications, substitutions, and alterations are possible without departing from the spirit and scope of the invention as described in the following claims.

What is claimed is:

1. A method of staining mitochondria with a fluorescent label, comprising:
   a) preparing an aqueous labeling solution containing a compound of the formula

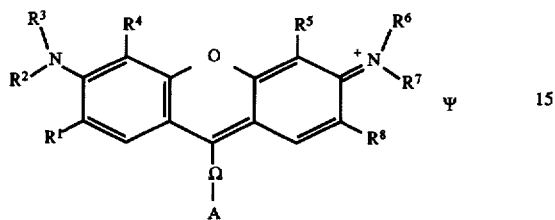

or of the formula

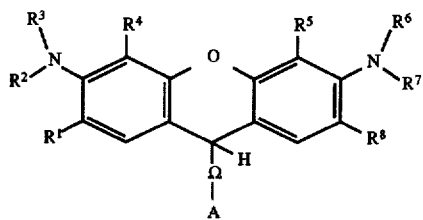

wherein a fused-ring system of the compound has
ring substituents $R^1$, $R^4$, $R^5$, and $R^8$ that are independently H, Cl, Br, I, $(CH_2)_nCH_3$, or $(CH_2)_nCO_2R^{13}$, where n is an integer from 0 to 15 and $R^{13}$ is an alkyl with 1–6 carbons; and amino substituents $R^2$, $R^3$, $R^6$, and $R^7$ that are independently H or $C_1$-$C_6$ alkyl;

or optionally any ring substituent in combination with an adjacent amino substituent independently forms an additional fused ring such that $R^1$ in combination with $R^2$, $R^3$ in combination with $R^4$, $R^5$ in combination with $R^6$, and $R^7$ in combination with $R^8$ is $(CH_2)_3$ or $(CH_2)_2$;

$\Omega$ is a covalent linkage that is a single covalent bond, or $\Omega$ is —Z—Y— where Z is attached to the fused ring system, and
Z is a covalent bond;
or Z is $(CH_2)_l$ where l=1–6;
or Z is

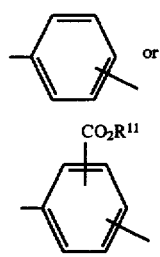

where $R^{11}$ is a hydrocarbon chain with 1–6 carbons that is branched, unbranched, saturated or unsaturated;
Y is a covalent bond or Y has the formula —$OCH_2R^{12}$—, —$OR^{13}$—, —$SR^{12}$—, —$SR^{13}$—,
—$NHCOCH_2R^{12}$—, —$NHCOR^{13}$—,
—$CONHCH_2R^{12}$—, —$CONHR^{13}$—,
$NHSO_2R^{12}$—, —$NHSO_2R^{13}$—,
—$NHCONHCH_2R_{12}$—, —$NHCONHR^{13}$—,
—$NHCSNHCH_2R_{12}$—, or —$NHCSNHR^{13}$—,
where $R^{12}$ is $(CH_2)_m$ and m=1–18, and $R^{13}$ is phenylene (—$C_6H_4$—);

such that Z and Y are not both covalent bonds;
A is an alkylating group that is
—$CR^9R^{10}X$, where $R^9$ and $R^{10}$ are independently H or $CH_3$, and X is Cl, Br, I, or —$OSO_2R^{16}$, where $R^{16}$ is $C_1$-$C_6$ alkyl; $C_1$-$C_6$ perfluoroalkyl; or $R^{16}$ is phenyl, or phenyl substituted one or more times by $C_1$-$C_6$ alkyl, $C_1$-$C_6$ perfluoroalkyl, Cl, Br, I, $NO_2$, or CN; or the alkylating group A is maleimidyl (—$NC_4H_2O_2$) or haloacetamido (—NH(C=O)—$CH_2$II) where II is Cl, Br or I;

$\Psi$ is a biologically compatible counterion,
where said compound is greater than 0 nM and less than about 500 nM in concentration; and
   b) incubating a sample, where the sample is isolated mitochondria or a cell containing intracellular mitochondria, in the labeling solution for a time sufficient to produce fluorescent labeled mitochondria.

2. A method, according to claim 1, wherein said compound has the formula

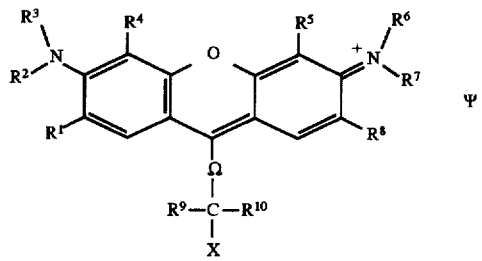

or of the formula

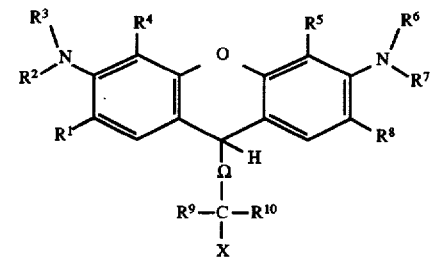

wherein X is Cl, Br, I, or —$OSO_2R^{16}$, where $R^{16}$ is $C_1$-$C_6$ alkyl, $C_1$-$C_6$ perfluoroalkyl; or $R^{16}$ is phenyl or phenyl substituted one or more times by $C_1$-$C_6$ alkyl, $C_1$-$C_6$ perfluoroalkyl, Cl, Br, I, $NO_2$ or CN.

3. A method, according to claim 1, wherein $\Omega$ is —Z—Y—, where

Z is

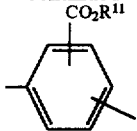

where $R^{11}$ is a hydrocarbon chain with 1–6 carbons that is branched, unbranched, saturated or unsaturated; and Y is a single covalent bond.

4. A method, according to claim 2, wherein $R^9$ and $R^{10}$ are H, and X is Cl, Br, or —$OSO_2R^{16}$, where $R^{16}$ is $C_1$–$C_2$ alkyl; $C_1$–$C_2$ perfluoroalkyl; phenyl; or phenyl substituted one or more times by $C_1$–$C_2$ alkyl, or $C_1$–$C_2$ perfluoroalkyl.

5. A method, according to claim 2, wherein $R^1$, $R^4$, $R^5$, and $R^8$ are H and $R^2$, $R^3$, $R^6$, and $R^7$ are independently H, $CH_3$ or $C_2H_5$; or $R^1$ in combination with $R^2$, $R^4$ in combination with $R^4$, $R^5$ in combination with $R^6$, and $R^7$ in combination with $R^8$ are $(CH_2)_3$.

6. A method, according to claim 1, wherein said compound has the formula

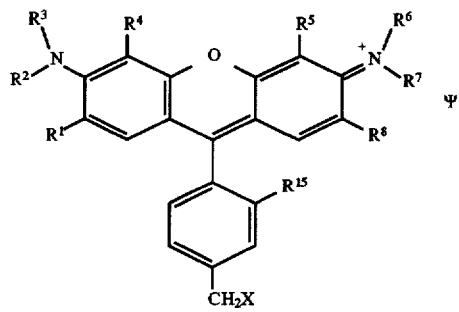

or of the formula

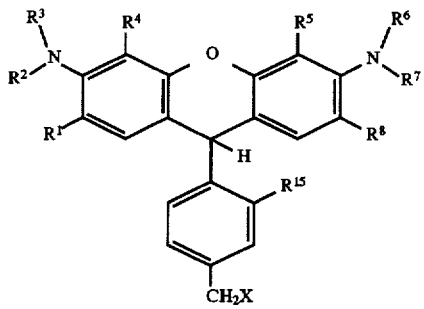

wherein
$R^1$, $R^4$, $R^5$, and $R^8$ are H; and $R^2$, $R^3$, $R^6$, and $R^7$ are independently H, $CH_3$, or $C_2H_5$;
or $R^1$ in combination with $R^2$, $R^4$ in combination with $R^4$, $R^5$ in combination with $R^6$, and $R^7$ in combination with $R^8$ are $(CH_2)_3$; and
$R^{15}$ is H or —$CO_2R^{11}$, where $R^{11}$ is a hydrocarbon chain with 1–6 carbons; and
X is Cl, Br, I, or —$SO_2R^{16}$, where $R^{16}$ is $C_1$–$C_2$ alkyl; $C_1$–$C_2$ perfluoroalkyl; phenyl; or phenyl substituted one or more times by $C_1$–$C_2$ alkyl or $C_1$–$C_2$ perfluoroalkyl.

7. A method, according to claim 6, wherein
$R^2$, $R^3$, $R^6$, and $R^7$ are $CH_3$;
$R^{15}$ is H; and
X is Cl.

8. A method, according to claim 6, wherein said compound has the formula

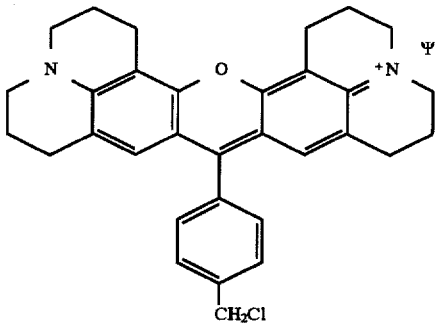

or of the formula

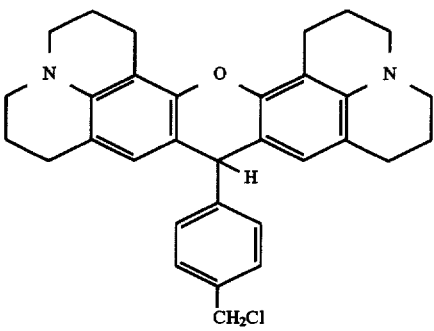

9. A method of analyzing mitochondrial function in a living eukaryotic cell or cells comprising
a) preparing an aqueous labeling solution containing a compound of the formula

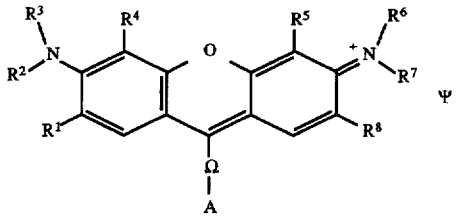

or of the formula

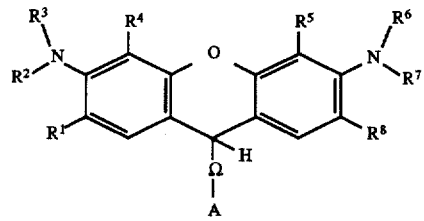

wherein a fused-ring system of the compound has ring substituents $R^1$, $R^4$, $R^5$, and $R^8$ that are independently H, Cl, Br, I, $(CH_2)_nCH_3$, or $(CH_2)_nCO_2R^{13}$, where n is an integer from 0 to 15 and $R^{13}$ is an alkyl with 1–6 carbons; and amino substituents $R^2$, $R^3$, $R^6$, and $R^7$ that are independently H or $C_1$–$C_6$ alkyl;
or optionally any ring substituent in combination with an adjacent amino substituent independently forms an additional fused ring such that $R^1$ in combination with $R^2$, $R^3$ in combination with $R^4$, $R^5$ in combination with $R^6$, and $R^7$ in combination with $R^8$ is $(CH_2)_3$ or $(CH_2)_2$; and $\Omega$ is a covalent linkage that is a single covalent bond, or $\Omega$ is —Z—Y— where Z is attached to the fused ring system, and Z is a covalent bond;

or Z is $(CH_2)_l$ where l=1–6;

or Z is

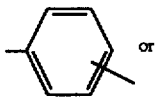

or

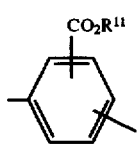

where $R^{11}$ is a hydrocarbon chain with 1–6 carbons that is branched, unbranched, saturated or unsaturated;

Y is a covalent bond or Y has the formula —$OCH_2R^{12}$—, —$OR^{13}$—, —$SR^{12}$—, —$SR^{13}$—, —$NHCOCH_2R_{12}$—, —$NHCOR_{13}$—, —$CONHCH_2R_{12}$—, —$CONHR_{13}$—, $NHSO_2R_{12}$—, —$NHSO_2R^{13}$—, —$NHCONHCH_2R^{12}$—, —$NHCONHR^{13}$—, —$NHCSNHCH_2R^{12}$—, or —$NHCSNHR^{13}$—, where $R^{12}$ is $(CH_2)_m$ and m=1–18, and $R^{13}$ is phenylene (—$C_6H_4$—);

such that Z and Y are not both covalent bonds; and

A is an alkylating group that is $CR^9R^{10}X$, where $R^9$ and $R^{10}$ are independently H or $CH_3$, and X is Cl, Br, I, or —$OSO_2R^{16}$, where $R^{16}$ is $C_1$–$C_6$ alkyl; $C_1$–$C_6$ perfluoroalkyl; or $R^{16}$ is phenyl, or phenyl substituted one or more times by $C_1$–$C_6$ alkyl, $C_1$–$C_6$ perfluoroalkyl, Cl, Br, I, $NO_2$, or CN; or the alkylating group A is maleimidyl (—$NC_4H_2O_2$) or haloacetamido (—NH(C=O)—$CH_2$II) where II is Cl, Br or I;

$\Omega$ is a biologically compatible counterion, where said compound is greater than 0 nM and less than about 500 nM in concentration;

b) incubating the eukaryotic cell or cells in the labeling solution for a time sufficient to produce fluorescent labeled mitochondria;

c) preparing the cell or cells for observation;

d) observing the cell or cells with means for detecting the fluorescent labeled mitochondria; and e) analyzing the function of said mitochondria, based on the presence or absence of mitochondrial fluorescence.

10. A method as described in claim 9, wherein said compound has the formula

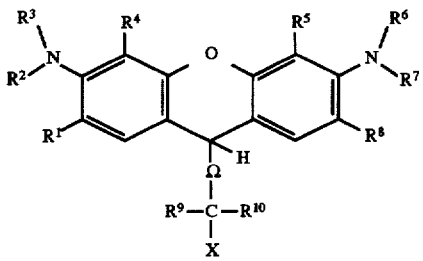

where the compound is greater than 50 nM and less than 500 nM in concentration.

11. A method as described in claim 9, wherein preparing the cell or cells for observation comprises fixing the cell or cells.

12. A method as described in claim 11, wherein preparing the cell or cells further comprises permeabilizing the cell or cells.

13. A method as in claim 9, further comprising adding an additional detection reagent to the cell or cells.

14. A method as in claim 9, wherein the observing is done using a microscope, fluorometer, microtiter plate reader, or flow cytometer.

15. A method as in claim 10, further comprising sorting the cells based on their fluorescent response.

16. A method, as claimed in claim 9, comprising a) preparing an aqueous labeling solution containing said compound of the formula

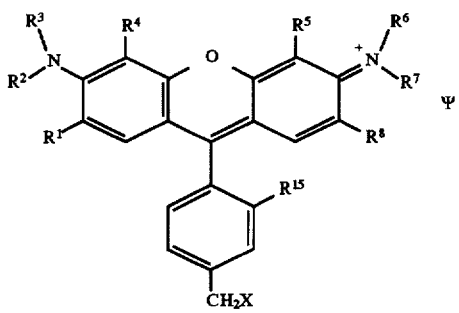

or of the formula

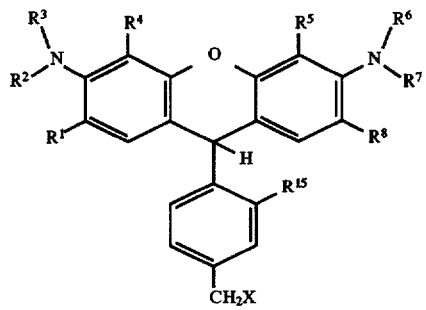

wherein $R^1$, $R^4$, $R^5$, and $R^8$ are H; and $R^2$, $R^3$, $R^6$, and $R^7$ are independently H, $CH_3$, or $C_2H_5$;

or $R^1$ in combination with $R^2$, $R^4$ in combination with $R^4$, $R^5$ in combination with $R^6$, and $R^7$ in combination with $R^8$ are $(CH_2)_3$; and $R^{15}$ is H or —$CO_2RH^{11}$, where $R^{11}$ is a hydrocarbon chain with 1–6 carbons that is branched, unbranched, saturated or unsaturated; and $R^9$ and $R^{10}$ are H, and X is Cl, Br, or —$OSO_2R^{16}$, where $R^{16}$ is $C_1$–$C_2$ alkyl; $C_1$–$C_2$ perfluoroalkyl; phenyl; or phenyl substituted one or more times by $C_1$–$C_2$ alkyl, $C_1$–$C_2$ perfluoroalkyl, where the compound is greater than 50 nM and less than 200 nM in concentration;

b) incubating the eukaryotic cell or cells in the labeling solution for a time sufficient to produce fluorescent labeled mitochondria;

c) washing, fixing, permeabilizing the cell or cells, and adding an additional detection reagent to the cell or cells; and d) observing the cell or cells with a means for detecting the fluorescent labeled mitochondria and additional detection reagent.

17. A method, as claimed in claim 16, where the additional detection reagent is a nucleic acid stain.

18. A method, as claimed in claim 16, where the additional detection reagent is a member of a specific binding pair that is an antibody, an avidin or streptavidin, or a biotinylated molecule.

19. A method, as claimed in claim 16, where the additional detection reagent is a probe that selectively accumulates in acidic organelles.

20. A method of determining foreign gene expression, comprising a) preparing an aqueous labeling solution containing a compound of the formula

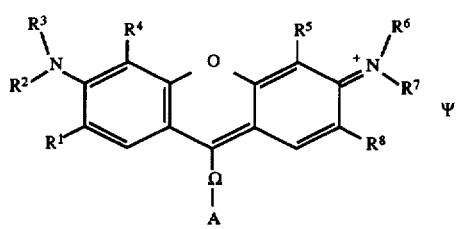

or of the formula

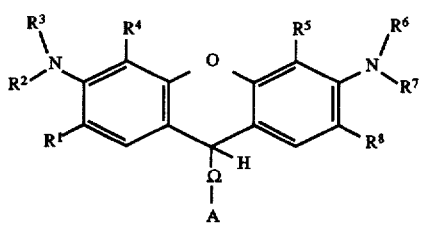

wherein a fused-ring system of the compound has ring substituents $R^1$, $R^4$, $R^5$, and $R^8$ that are independently H, Cl, Br, I, $(CH_2)_nCH_3$, or $(CH_2)_nCO_2R^{13}$, where n is an integer from 0 to 15 and $R^{13}$ is an alkyl with 1–6 carbons; and amino substituents $R^2$, $R^3$, $R^6$, and $R^7$ that are independently H or $C_1$–$C_6$ alkyl;

or optionally any ring substituent in combination with an adjacent amino substituent independently forms an additional fused ring such that $R^1$ in combination with $R^2$, $R^3$ in combination with $R^4$, $R^5$ in combination with $R^6$, and $R^7$ in combination with $R^8$ is $(CH_2)_3$ or $(CH_2)_2$; and Ω is a covalent linkage that is a single covalent bond, or Ω is —Z—Y— where Z is attached to the fused ring system, and Z is a covalent bond;

or Z is $(CH_2)_I$ where I=1–6;

or Z is

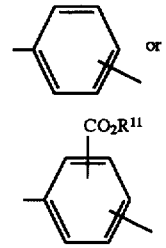

where $R^{11}$ is a hydrocarbon chain with 1–6 carbons that is branched, unbranched, saturated or unsaturated;

Y is a covalent bond or Y has the formula —$OCH_2R^{12}$—, —$OR^{13}$—, —$SR^{12}$—, —$SR^{13}$—, —$NHCOCH_2R^{12}$—, —$NHCOR^{13}$—, —$CONHCH_2R^{12}$—, —$CONHR_{13}$—, $NHSO_2R^{12}$—, —$NHSO_2R^{13}$—, —$NHCONHCH_2R^{12}$—, —$NHCONHR^{13}$—, —$NHCSNHCH_2R^{12}$—, or —$NHCSNHR^{13}$—, where $R^{12}$ is $(CH_2)_m$ and m=1–18, and $R^{13}$ is phenylene (—$C_6H_4$—);

such that Z and Y are not both covalent bonds; and

A is an alkylating group that is $CR^9R^{10}X$, where $R^9$ and $R^{10}$ are independently H or $CH_3$, and X is Cl, Br, I, or —$OSO_2R^{16}$, where $R^{16}$ is $C_1$–$C_6$ alkyl; $C_1$–$C_6$ perfluoroalkyl; or $R^{16}$ is phenyl, or phenyl substituted one or more times by $C_1$–$C_6$ alkyl, $C_1$–$C_6$ perfluoroalkyl, Cl, Br, I, $NO_2$, or CN; or the alkylating group A is maleimidyl (—$NC_4H_2O_2$) or haloacetamido (—NH(C=O)—$CH_2$II) where II is Cl, Br or I;

Ω is a biologically compatible counterion, where said compound is greater than 0 nM and less than about 500 nM in concentration;

b) incubating the eukaryotic cell or cells in the labeling solution for a time sufficient to produce fluorescent labeled mitochondria;

c) washing, fixing, and permeabilizing the cell or cells, and adding an additional detection reagent to the cell or cells, wherein said additional detection reagent fluorescently labels a protein that is present in the cell as a result of expression of a transfected gene, or said additional detection reagent fluorescently labels an antibody against said protein; and d) observing the cell or cells with a microscope.

\* \* \* \* \*

UNITED STATES PATENT AND TRADEMARK OFFICE
CERTIFICATE OF CORRECTION

PATENT NO. : 5,686,261
DATED : Nov. 11, 1997
INVENTOR(S) : Zhang et al.

It is certified that error appears in the above-indentified patent and that said Letters Patent is hereby corrected as shown below:

At Col. 13, line 8 of Table 3, "mouse antibody anti-mouse–blotin" should be -- mouse antibody anti-mouse–biotin --.

At Col. 25, line 60, "X is Cl, Br, I, or $-SO_2R^{16}$" should be -- X is Cl, Br, I, or $-OSO_2R^{16}$ --.

At Col. 27, line 51, "$\Omega$ is a biologically compatible counterion." should be -- $\Psi$ is a biologically compatible counterion--.

At Col. 28, line 65, "$R^{15}$ is H or $-CO_2 RH^{11}$" should be -- $R^{15}$ is H or $-CO_2R^{11}$ --.

At Col. 30, line 28, "$-CONHR_{13}-$" should be -- $-CONHR^{13}-$ --.

At Col. 30, line 45, "$\Omega$ is a biologically compatible counterion," should be -- $\Psi$ is a biologically compatible counterion--.

Signed and Sealed this

Fourteenth Day of December, 1999

Attest:

Q. TODD DICKINSON

*Attesting Officer*

*Acting Commissioner of Patents and Trademarks*